United States Patent [19]

Engelman

[11] Patent Number: 5,725,486

[45] Date of Patent: Mar. 10, 1998

[54] ORTHOTIC LEG ELEVATOR

[76] Inventor: Ian Engelman, 27 Valley View Rd., Newtown, Conn. 06470

[21] Appl. No.: 610,494

[22] Filed: Mar. 4, 1996

[51] Int. Cl.⁶ .................................................. A61F 5/00
[52] U.S. Cl. .......................... 602/5; 602/23; 128/882; 5/648
[58] Field of Search ................................. 128/877, 882, 128/845; 602/1, 5, 23; 5/327, 624

[56] References Cited

U.S. PATENT DOCUMENTS

| | | | |
|---|---|---|---|
| 3,931,654 | 1/1976 | Spann | 5/327 |
| 3,946,451 | 3/1976 | Spann | 5/327 |
| 4,805,605 | 2/1989 | Glassman | 602/24 |
| 4,940,066 | 7/1990 | Santilli et al. | 128/882 |
| 5,046,487 | 9/1991 | Scott | 128/882 |
| 5,584,303 | 12/1996 | Walle | 128/882 X |

FOREIGN PATENT DOCUMENTS

332960  9/1989  European Pat. Off. ............... 602/15

*Primary Examiner*—Richard J. Apley
*Assistant Examiner*—Kim M. Lee
*Attorney, Agent, or Firm*—Michael Ebert

[57] ABSTRACT

An orthotic leg elevator for elevating the leg of a subject during a post-operative period or in other situations in which it is necessary to avoid direct contact between the leg and a bed or other surface, or to raise the leg with respect to a surface. The leg elevator includes a rectangular block whose top side has formed therein a concave trough extending the length of the block to cradle the leg of the subject so that his foot is then adjacent the front end of the trough. Nested in the trough at its rear end is a knee-supporting piece which underlies and conforms to the knee joint. Secured to the block are three detachable straps adapted to engage the cradled leg at spaced positions. The first strap engages the leg above the ankle; the second at an intermediate position between the ankle and the knee, and the third just above the knee, thereby immobilizing the leg. To accommodate the leg elevator to different situations, attachable to the underside of the block are slabs or wedges which serve to adjust the height of the elevator, or the relative heights of the knee and foot of the cradled leg, or the inclination of the block relative to the horizontal plane.

9 Claims, 8 Drawing Sheets

ORTHOTIC LEG ELEVATOR

BACKGROUND OF INVENTION

1. Field of Invention

This invention relates generally to orthotic devices, and more particularly to an orthotic leg elevator useable in a post-operative period in which the foot must be kept off the ground, or in diagnostic imaging in the course of which the leg position must be fixed, or in other situations in which it is necessary to avoid direct contact between the leg and a bed or other surface.

2. Status of Prior Art

Orthotics is a science dealings with the use of specialized mechanical devices to support or supplement weakened or abnormal joints or limbs. The present invention is concerned with an orthotic device adapted to elevate the leg of a subject so that it makes no direct contact with a bed or other surface.

In order to support the limb of a bed-ridden hospitalized patient to prevent the formation of ulcers and bed sores on the heel which occur when the heel of the patient is allowed to make contact with the bed for a prolonged period, the patents to Spann U.S. Pat. Nos. 3,946,451 and 3,931,654 disclose a limb support formed by a block of resilient polyurethane foam material having formed in its top side an arcuate groove extending along its length to cradle the limb.

The Scott U.S. Pat. No. 5,046,487 discloses a leg elevator for use following a surgical procedure to prevent the formation of blood clots in the patient. The Scott elevator is formed by a block having a trough at its upper side to receive the leg. The rear end of the block is sloped so that the knee of the leg lies at the junction of the trough and the slope, and the upper limb then runs down the slope. Straps are provided to secure the leg to the block.

The Pecheaux U.S. Pat. No. 4,323,060 discloses an elaborate elevator mechanism for supporting a leg at various positions in the course of orthopedic treatment. An adjustable leg elevator is also disclosed in the Andrews U.S. Pat. No. 4,336,796.

The leg elevators disclosed these prior art patents are each intended for a specific application, such as to prevent the heel of patient from making contact with a bed. The need exists for an orthotic leg elevator usable in a broad range of applications, all of which require that the leg of the subject be immobilized and isolated from a supporting surface, such as a bed or floor.

And the need also exists for a leg elevator that can be accommodated to legs of different shape and size as well as to different applications, such as in post-operative situations in which is necessary to minimize edema or swelling, or to keep the foot off the ground. Another situation in which a need exist for a leg elevator, is when it is necessary to flatten the lower back while supine and thereby avoid back pain. Also in diagnostic imaging, the position of the leg must be maintained while the image is being taken.

A further object of the invention is to provide a leg elevator which is strapped to the leg of a subject and makes it possible for the subject to sit confortably in a chair, with the foot of the subject then out of contact with the floor on which the chair is placed.

Yet another object of the invention is to provide a foot isolator attachable to the front end of the block, to go over the foot of the leg cradled in the block whereby when the subject is lying in bed, he may be covered with a blanket which is kept out of contact with the foot by the foot escalator.

Still another object of the invention is to provide a plantarflexion stop which permits a subject to dorsiflex his foot to a given degree and to then maintain it at that position.

Briefly stated, these objects are attained by an orthotic leg elevator for raising the leg of a subject during a post-operative period or in other situations in which it is necessary to avoid direct contact between the leg and a bed or other surface. The leg elevator includes a light-weight rectangular block preferably formed of rigid foam plastic material whose top side has formed therein a concave trough extending the length of the block to cradle the leg of the subject so that his foot is adjacent the front end of the trough.

Nested in the trough at its rear end is a knee-supporting piece which underlies and conforms to the knee joint whereby the upper limb of the subject then extends beyond the block. Secured to the block are three detachable straps adapted to engage the cradled leg at spaced positions. The first

SUMMARY OF INVENTION

In view of the foregoing, the main object of this invention is to provide an orthotic leg elevator applicable to diverse situations in which it is necessary to avoid direct contact between the leg of a subject and a bed or other supporting surface.

More particularly, an object of this invention is to provide a leg elevator that includes a rectangular block having formed in its top side a concave trough that runs the length of the block to cradle the leg of a subject, the block having secured thereto detachable straps adapted to engage the leg at three positions and thereby immobilize the leg.

A significant advantage of a leg elevator in accordance with the invention is that it may be accommodated to legs of different size and shape as well as to different applications.

Also an object of the invention is to provide a leg elevator of the above type which is supplied with removable pieces that fit into the trough cradling the leg the pieces affording support under the knee and under the Achilles tendon of the leg, the pieces conforming the trough to the contours of the leg.

Another object of this invention is to provide wedges or slabs which are placeable under the leg elevator block to adjust the height of elevation, or the relative heights of the knee and foot of the leg cradled in the block, or the inclination of the block relative to the horizontal plane. strap engages the leg above the ankle; the second, at an intermediate position between the ankle and the knee, and the third just above the knee, thereby immobilizing the leg.

To accommodate the leg elevator to different situations, attachable to the underside of the leg are slabs or wedges which serve to adjust the height of the elevator, or the relative heights of the knee and foot of the cradled leg, or the inclination the block relative to the horizontal plane.

BRIEF DESCRIPTION OF DRAWINGS

For a better understanding of the invention reference is made to the detailed description to follow which is to be read in conjunction with the accompanying drawings wherein.

DETAILED DESCRIPTION OF INVENTION

The Basic Leg Elevator

Referring now to FIGS. 1 to 6, there is shown in these figures a preferred embodiment of a leg elevator in accordance with the invention whose main component is a block 10 having a rectangular cross-section and a length somewhat longer than to that of a typical adult leg. Block 10 is fabricated of a light-weight material possessing good structure strength such as a rigid high-density polyurethane foam or PVC foam. In practice, the block may be formed of Balsa wood or of aluminum.

The leg elevator is intended for a wide range of adult leg sizes, and if the subject has a relatively short leg, the subject's leg when cradled in the elevator will not reach the front end of the block, whereas his knee will be positioned adjacent the rear end thereof. With a subject having a longer leg, his knee will again be adjacent the rear end of the block but his foot will be closer to its front end.

Figure 5:
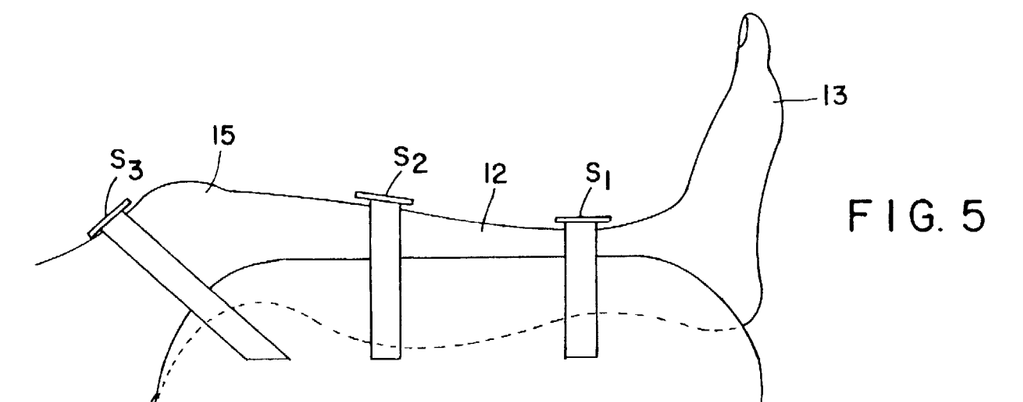
FIG. 5 illustrates a leg strapped to the leg elevator.

The top side of block 10 has formed therein a concave trough 11 running the full length of the block to cradle the leg 12 of the subject, as shown in FIG. 5. Hence the foot 13 of the subject is then adjacent the front end of the block and projects upwardly therefrom. Nested in the rear end of block 10 is a knee-supporting piece 14, shown separately in FIG. 3, preferably molded of the same foam plastic material as the block material so that this piece conforms to the trough and is snugly received therein in frictional engagement with the trough. Piece 14 is shaped so that its upper surface conforms to the contour of the knee joint.

Figure 6:
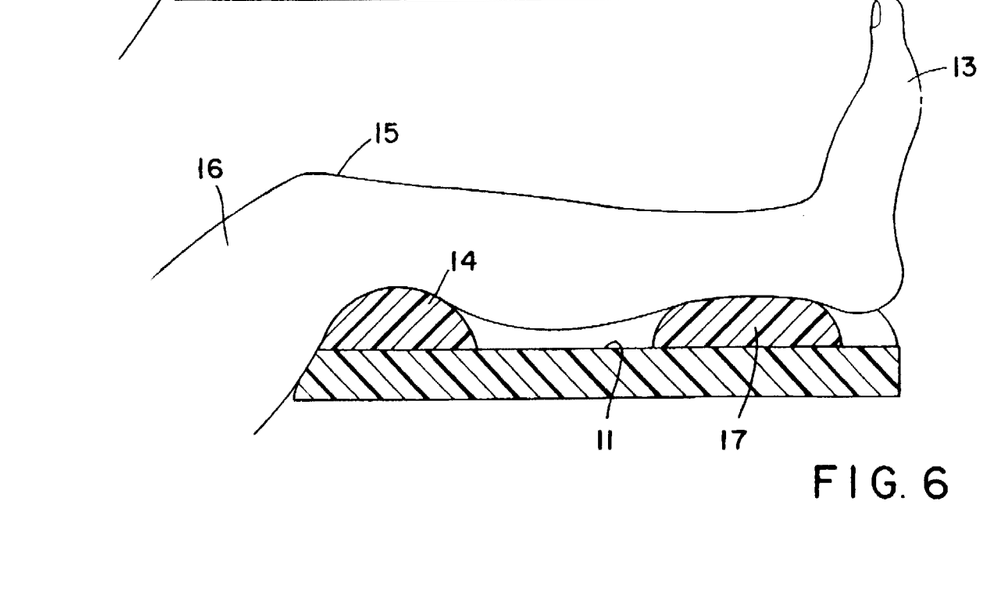
FIG. 6 shows the relationship of the cradled leg to the two supporting pieces.

As shown in FIG. 6, piece 14 which supports the knee 5 of the subject's leg cradled in the trough underlies the knee joint. Hence the limb 16 of the subject extends beyond block 10 and the knee cap projects above the rear end of the block.

Figure 4:
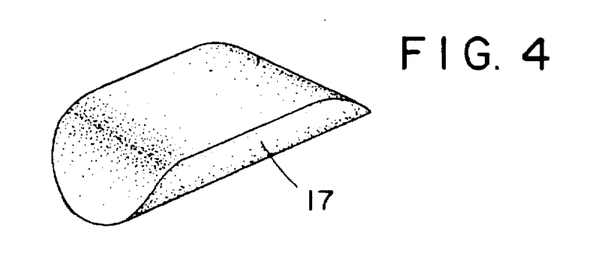
FIG. 4 is a perspective view of the Achilles tendon-supporting piece included in the leg elevator.

Also inserted in trough 11 of the leg elevator is an Achilles tendon support piece 17, as shown separately in FIG. 4. The Achilles tendon is the large tendon connecting the heel bone to the calf muscle of the leg. In order to comfortably cradle the leg in the leg elevator, the Achilles tendon must be supported by piece 17, as shown in FIG. 6. Piece 17 which is molded of foam plastic material to conform to the curvature of the trough is provided with a flat top surface which underlies the Achilles tendon of the leg cradled in the elevator. Hence the two pieces 14 and 17 nested in trough 11 act to conform the trough to the contours of the leg cradled therein.

Figure 1:
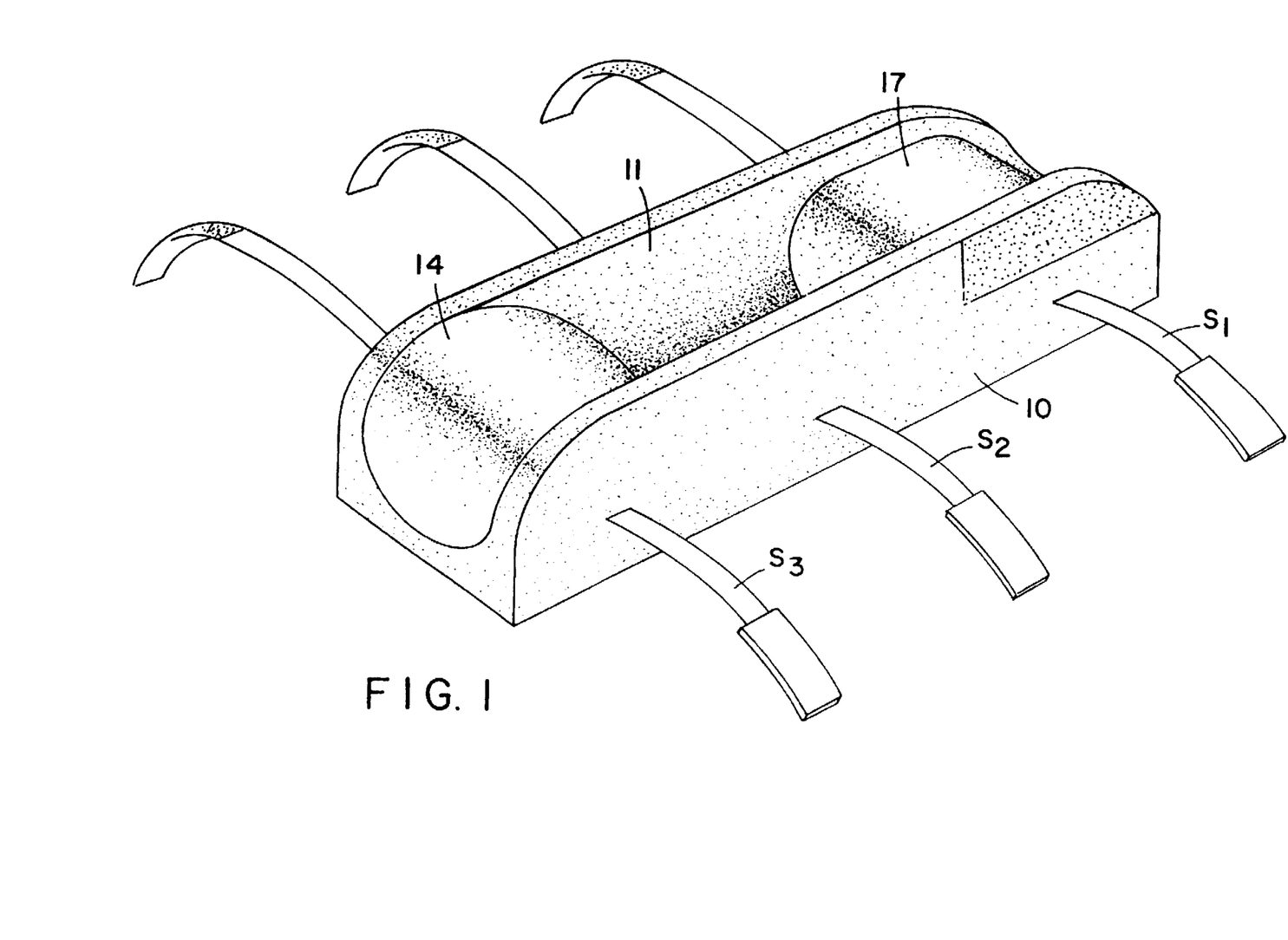
FIG. 1 is a perspective view of a basic leg elevator in accordance with the invention.
Figure 2:
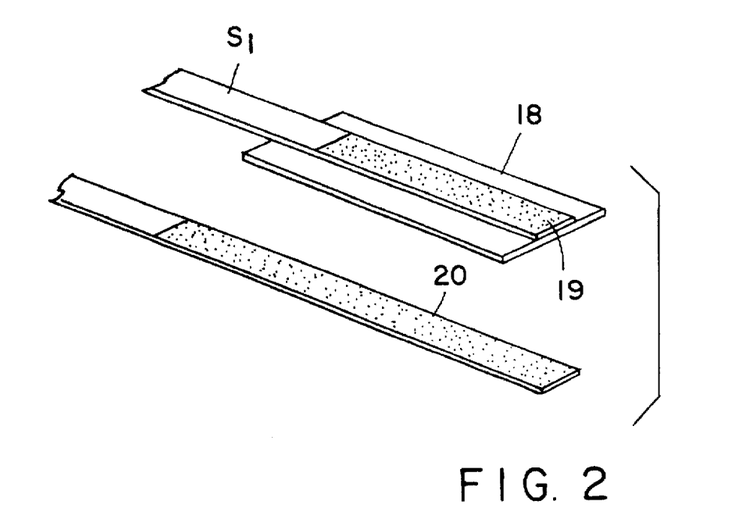
FIG. 2 illustrates the opposing ends of one of the straps included in the leg elevator, which ends are provided with fastener components of a Velcro fastener.
Figure 3:
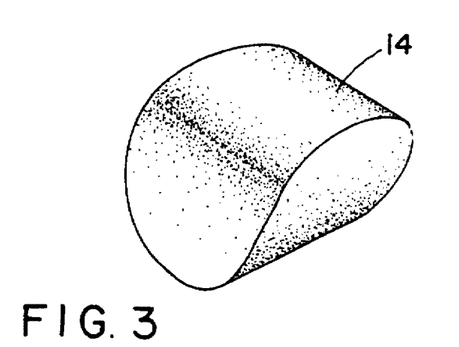
FIG. 3 is a perspective view of the knee-supporting piece included in the leg elevator.

Secured to block 10 are three detachable fabric straps $S_1$, $S_2$ and $S_3$. One end of each strap, as shown in FIG. 2 in connection with Strap $S_1$, has sewn or otherwise attached to its underside a rectangular protective pad 18 of flexible foam plastic material.

Anchored on the exposed side of the same strap end is a strip 19 of the male component of a Velcro fastener. The underside of the other end of strap $S_1$ has anchored thereon the female component 20 of the Velcro fastener.

In a Velcro fastener, the male component is formed by a uniform array of minute stiff nylon hooks, whereas the female component is formed by a pile of tiny soft nylon loops. When the two components are pressed together, the male component hooks become embedded in the female component loops, thereby joining the component. To disconnect the components, the male component is peeled off the female component. In practice, instead of Velcro fasteners, buckles or other fastening means may be used in conjunction with the straps.

As illustrated in FIG. 5, when a subject's leg 12 is cradled in leg elevator block 10, strap $S_1$ is then strapped above the ankle and strap $S_2$ is strapped at an intermediate position between the ankle and the knee cap, preferably at the medial flare of the tibia. Strap $S_3$ is strapped about just above the cap of knee 15.

These three straps function to firmly secure the cradled leg to the leg elevator regardless of the subject's activity. Thus the leg remains secure while the subject is sleeping, or is sitting in a chair, or is ambulatory. When the subject is lying supine, his lower back is flattened and the leg elevator then acts to avoid back pain. In a post-surgery situation, the leg elevator acts to minimize swelling of the leg, an in post-foot surgery, the leg elevator keeps the foot off the ground. In diagnostic imaging of the leg, it is then desirable to place the leg in the leg elevator, for the elevator functions to fix the position of the leg while taking an image.

Chair Use

It is not necessary when a subject has a leg elevator strapped to his leg, that he then be in a supine position, for the subject may be able to sit in a chair while his foot or leg is undergoing healing in a post-operative period.

Figure 7:
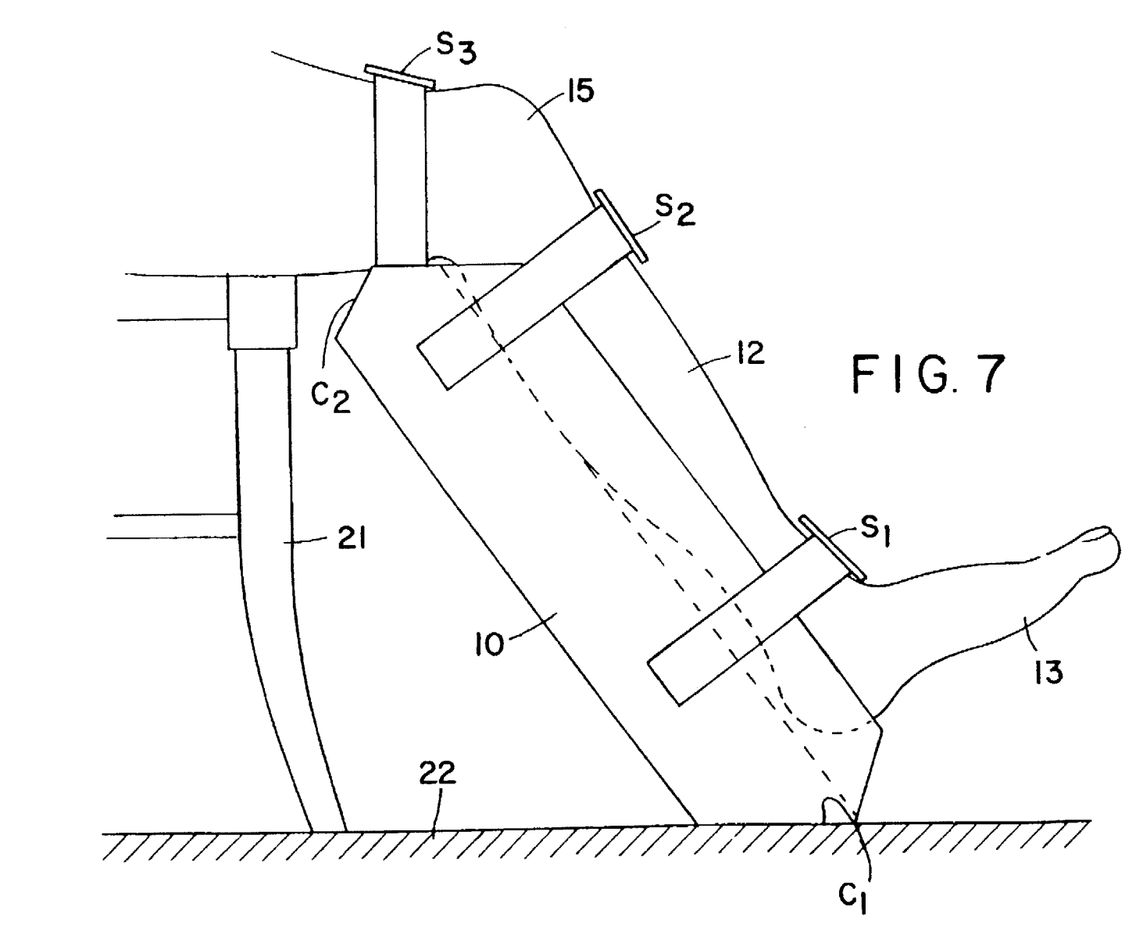
FIG. 7 shows a leg elevator for use by a subject in a chair sitting position.

But when the subject is sitting in a chair, the leg elevator strapped to his leg must accommodate itself to the subject's sitting position. To facilitate using the leg elevator in a chair sitting mode, as shown in FIG. 7, the proximal and distal ends of the leg elevator are provided with angled cuts $C_1$ and $C_2$.

When the subject is sitting in chair 21, and the leg elevator is then at an upright angle to the ground surface 22, the angle of cut $C_1$ is such that the front end of the leg elevator lies flat against the floor and the angle of cut $C_2$ is such that the rear end of the leg elevator lies flat against the side of the chair.

In practice, the leg elevator may also be provided with angled cuts at its front end so as not to obstruct knee movement during ambulation of the subject with a walker or crutches. Thus block 10 is not limited to supine situations, for its ends are shaped to accommodate situations in which the block assumes an upright position.

Plantarflexion Stop

When a subject's leg is strapped to the leg elevator, he is then free to flex his foot 13 which projects upwardly. In some instances it is necessary to provide a plantarflexion stop which permits the subject to dorsiflex his foot 13 to a given degree and to then maintain it at that position.

Figures 8, 9:
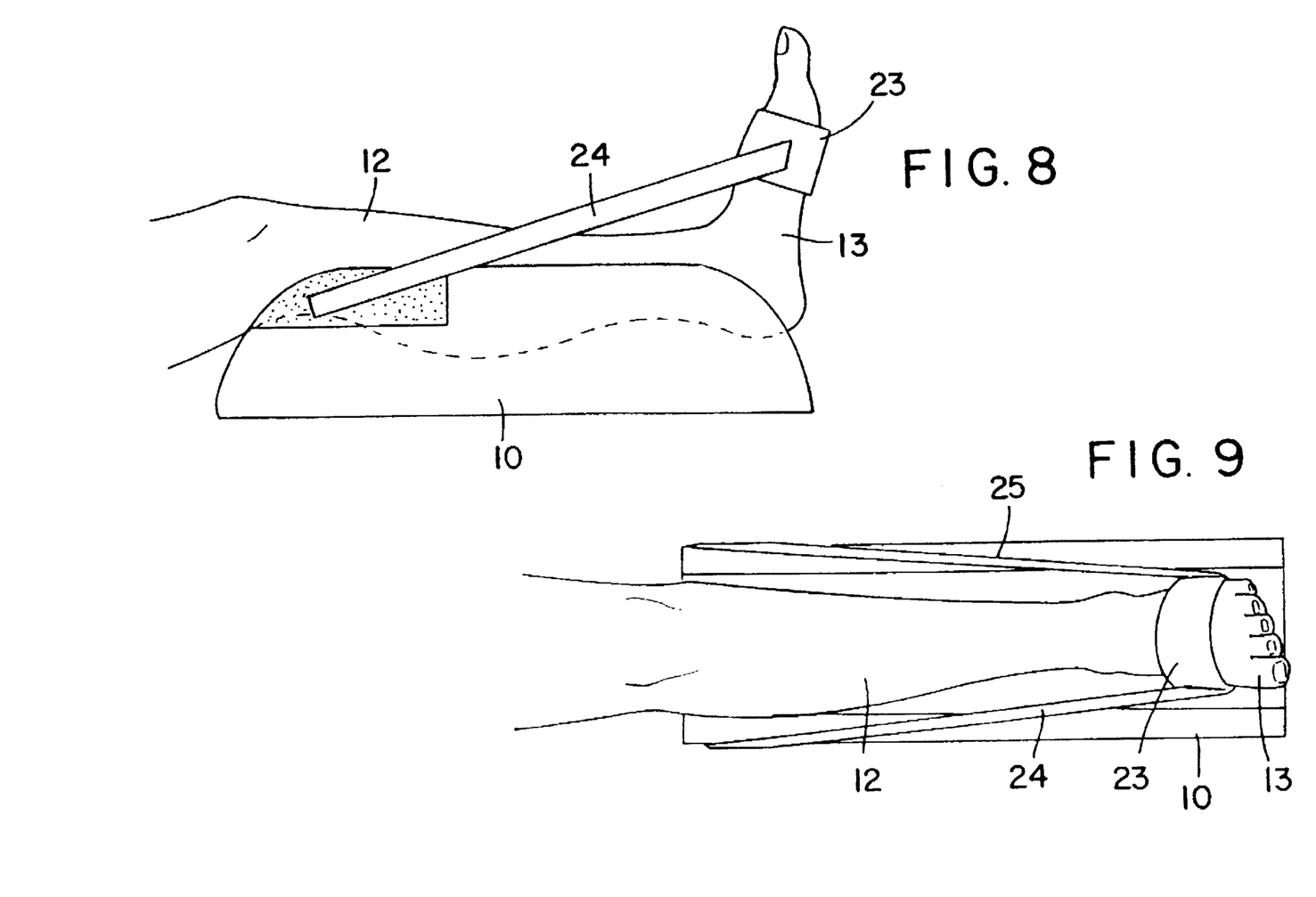
FIG. 8 is a side view of a plantarflexion stop coupled to the foot of the leg strapped in the leg elevator.
FIG. 9 is a top view of the plantarflexion stop.

For this purpose, as shown in FIGS. 8 and 9, a collar 23 is provided that fits above the foot below the toes. Collar 23 may be formed of a strip of fabric material which can be wrapped about the foot, the strip being provided with Velcro fastener components to convert the wrapping to a collar. Attached to collar 23 is a pair of fabric straps 24 and 25 carrying at its free ends female Velcro components which can be pressed against male components anchored on opposing sides of elevator block 10 to maintain the foot at a desired dorsiflex position.

Thus to install the plantarflexion stop, collar 23 is first coupled to the foot 13 and the foot is dorsiflexed to a desired degree. Then the straps 24 and 25 are fastened to the sides of block 10 to maintain the dorsiflex position.

Foot Isolator

When a subject wearing a leg elevator in accordance with the invention, lies in a bed, it is then the usual practice to cover the subject with a blanket to keep him warm. Since the foot 13 projects upwardly from the elevator, the blanket will then make contact with the toes of the foot and may apply excessive pressure thereto. This is not acceptable in those situations in which the foot is undergoing a healing process.

Figures 10, 11:
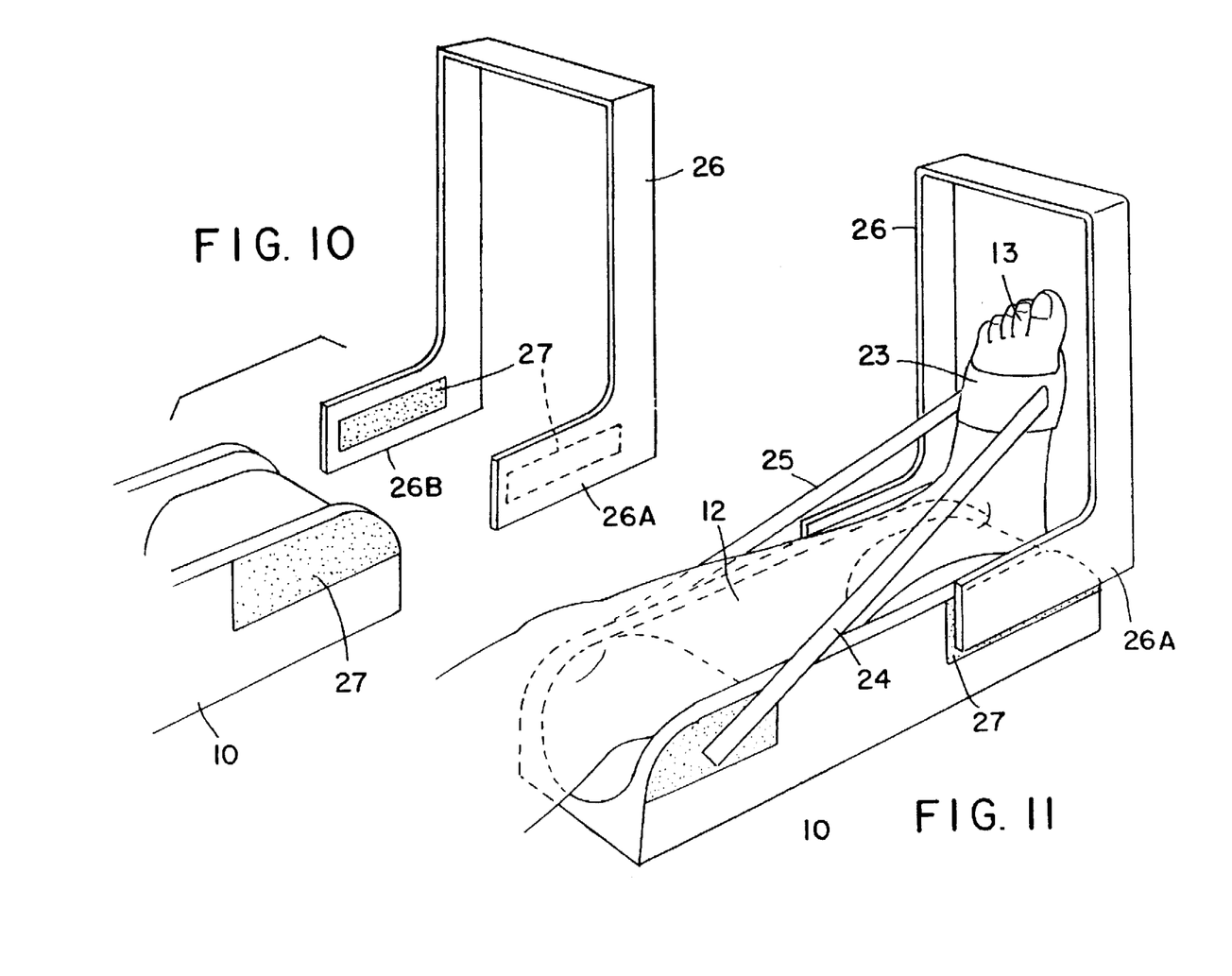
FIG. 10 shows a foot isolator for the leg elevator.
FIG. 11 shows the foot isolator attached to the leg elevator.

To avoid such undue pressure, a foot isolator 26 is provided, as shown in FIGS. 10 and 11, formed by a U-shaped arch having horizontal side branches 26A and 26B extending from the base of the arch. The side branches are provided on their inner surface with Velcro male patches 27 that engage corresponding female patches secured to the opposite sides of elevator block 10.

Thus, as shown in FIG. 11, when the foot isolator is installed on block 10, foot 13 of leg 12 cradled in the block lies within the protective arch 26. And when a cover is thrown over the leg, the cover overlies arch 26 and therefore makes no contact with the toes of foot 13 and applies no pressure thereto.

Height and other Adjustments

Depending on the shape and size of the leg strapped in the leg elevator block 10 and the particular use to which the elevator is put, it may be necessary to more or less increase the height of the elevator and into other ways alter the orientation of the block relative to a horizontal ground surface.

Figure 12:
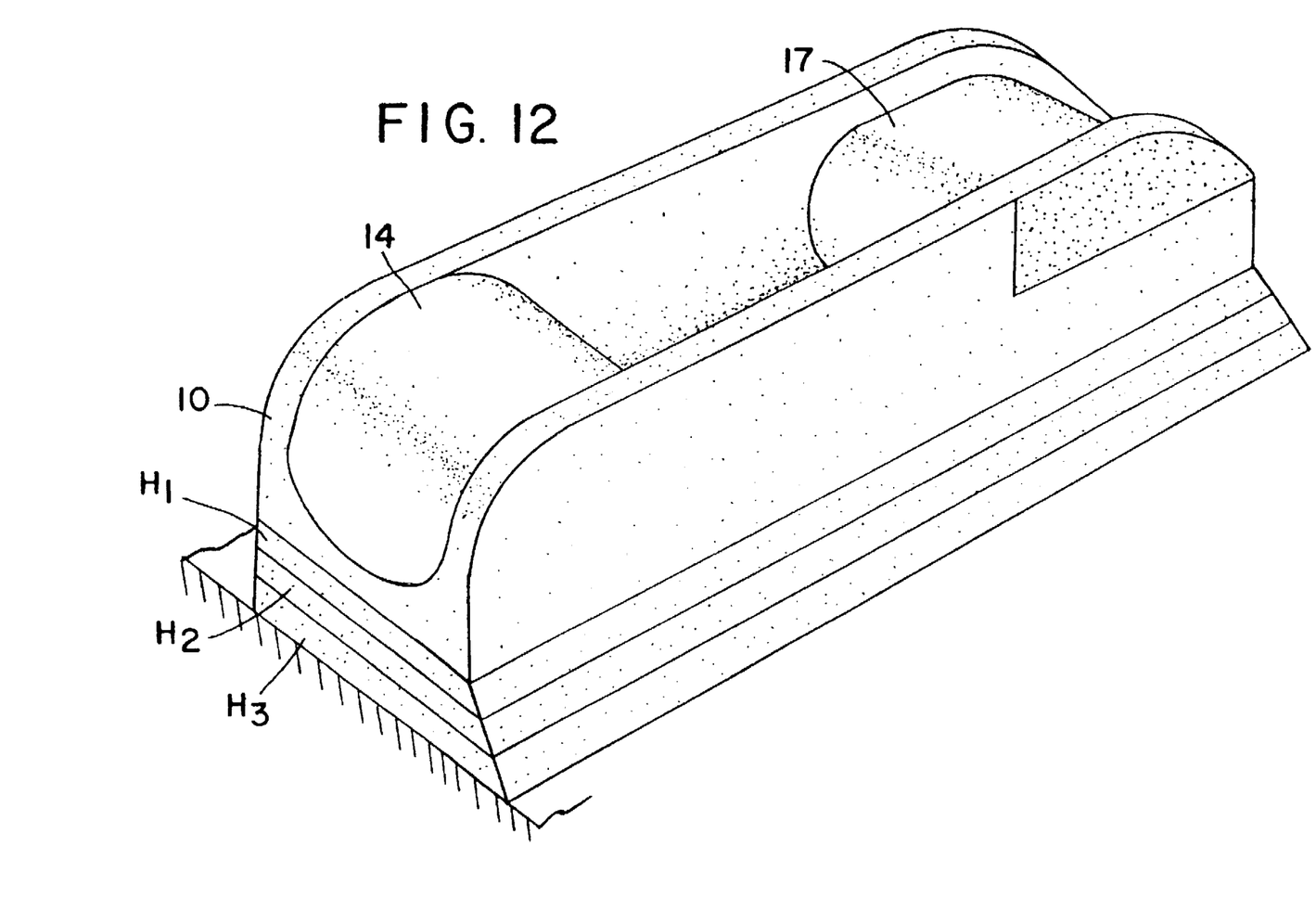
FIG. 12 shows a set of slabs adapted to raise the height of the leg elevator.

To effect height adjustment, a set of height adjusting slabs $H_1$, $H_2$ and $H_3$ are provided, as shown in FIG. 12. These slabs all have the same thickness (i.e. 5 cm), but are progressively wider so that their stability is maintained laterally. The slabs may be formed of the same foam plastic material as block 10.

Slab $H_1$ is joined to the underside of elevator block 10 by a flat Velcro fastener, slab $H_2$ is joined to the underside of slab $H_1$ by a Velcro fastener, and slab $H_3$ is joined to the underside of slab $H_2$ by a Velcro fastener. The number of slabs used in a given situation depends on the desired degree of height adjustment.

In FIG. 5, elevator block 10 is placed on a flat horizontal surface so that leg 12 strapped in the trough of the block is generally horizontal, with the foot 13 projecting upwardly from the horizontal plane and the cap of knee 15 bulging upwardly from this plane. In some situations it is desireable to change the relative heights of the knee and the foot of the leg strapped in the elevator block.

Figures 13, 14:
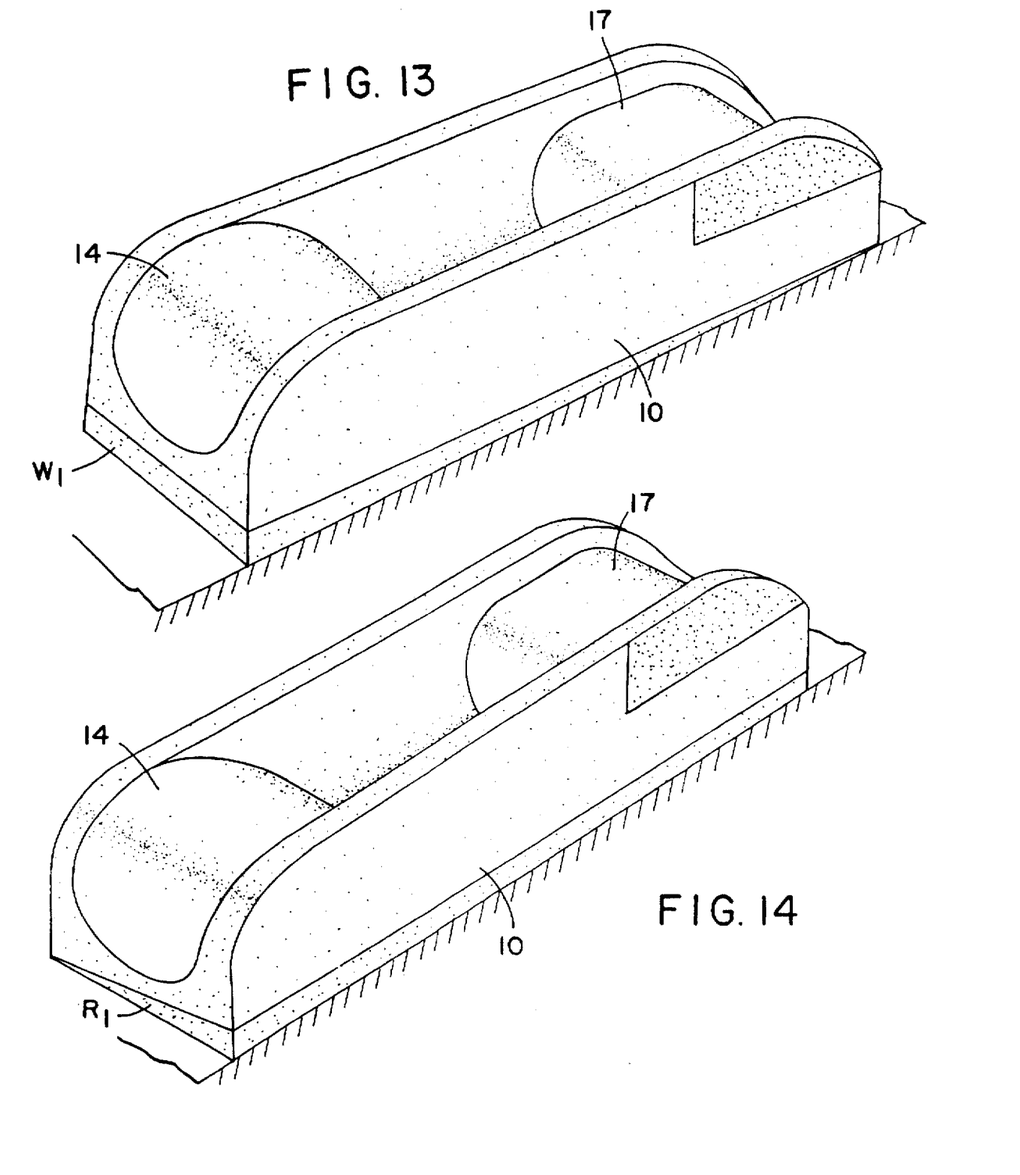
FIG. 13 shows a wedge adapted to incline the leg elevator relative to a horizontal surface.
FIG. 14 shows a wedge adapted to rotate the leg elevator about its longitudinal axis relative to a horizontal surface.

For this purpose there is provided a set of wedges each having a different wedge angle. One such wedge $W_1$ is shown in FIG. 13. Wedge $W_1$ which underlies block 10 has the same length and is secured to the underside of the block by a Velcro fastener. As a result, the rear end of the block 10 is raised above the horizontal surface in which it is placed but front rear end is not, so that the height of foot 13 which is adjacent the front end is raised but the knee adjacent the rear end of the block is not.

In some instances it may be desirable to rotate block 10 placed on a horizontal surface as in FIG. 5, so that block 1 then lies in a plane inclined with respect to this surface.

For purposes of rotating the position of the block so that it lies in an inclined plane, a set of wedges are provided, such as wedge $R_1$ shown in FIG. 14. Wedge $R_1$, when placed under elevator block 10 and joined thereto by a Velcro fastener, acts to tilt the block about its longitudinal axis to a degree depending on the acute angle of the wedge.

While there have been shown and disclosed preferred embodiments of the orthotic leg elevator in accordance with the invention, it is to be understood that many changes may be made therein without departing from the spirit of the invention.

I claim:

1. An orthotic leg elevator for keeping a leg of a human subject out of contact with a bed or other surface, said elevator comprising:

A. a rectangular block of predetermined length having a top side and a bottom side, said top side having a concave trough that extends the length of the block in parallel to the bottom side to cradle the leg of the subject received therein so that the foot is then adjacent a front end of the block and projects thereabove, and his knee is then adjacent a rear end of the block;

B. a removable Achilles tendon supporting arched piece nested adjacent the front end of the trough and underlying the Achilles tendon of the leg cradled in the trough whereby a front portion of the leg extends above the top side of the block;

C. a removable knee-supporting arched piece nested adjacent the rear end of the trough and underlying the joint of the knee whereby a rear portion of the leg extends above the top side of the block and the knee cap projects above the block; and D. detachable straps to secure the leg to the block at spaced apart positions; one of said straps being adapted to engage the leg just above the ankle, a second of said straps being adapted to engage the leg at a position intermediate the ankle and the knee and a third of said straps being adapted to engage the leg above the knee to firmly secure the leg to the leg elevator regardless of the activity of the subject.

2. A leg elevator as set forth in claim 1, in which the block is molded of rigid foam plastic material.

3. A leg elevator as set forth in claim 1, in which each strap is provided at its ends with the male and female components of a Velcro fastener.

4. A leg elevator as set forth in claim 1, including a slab attachable to the underside of the block to raise its height.

5. A leg elevator as set forth in claim 1, including a wedge attachable to the underside of the block to incline the block relative to the horizontal plane.

6. A leg elevator as set forth in claim 1, including a wedge attachable to the underside of the block to rotate it about the longitudinal axis of the block.

7. A leg elevator as set forth in claim 1, further including a collar adapted to engage the foot projecting above the block and, wherein a strap extending from the collar and attachable to opposing sides of the block to maintain the foot at a desired dorsiflex position.

8. A leg elevator as set forth in claim 1, further including a foot isolator attachable to opposite sides of the block to isolate the foot from a cover placed over the leg elevator.

9. A leg elevator as set forth in claim 8, in which the isolator includes an arch which goes over the upwardly projecting foot.

* * * * *